United States Patent [19]
Vaitekunas et al.

[11] Patent Number: 6,004,335
[45] Date of Patent: Dec. 21, 1999

[54] ULTRASONIC HEMOSTATIC AND CUTTING INSTRUMENT

[75] Inventors: Jeffrey J. Vaitekunas, West Chester; Louis F. Cosentino; Richard VanZandt, both of Cincinnati, all of Ohio

[73] Assignee: Ethicon Endo-Surgery, Inc., Cincinnati, Ohio

[21] Appl. No.: 08/600,435

[22] Filed: Feb. 12, 1996

Related U.S. Application Data

[63] Continuation of application No. 08/284,338, Aug. 2, 1994, abandoned.

[51] Int. Cl.⁶ .................................................. A61B 17/36
[52] U.S. Cl. .............................. 606/169; 606/1; 606/205; 606/142; 604/22; 227/180.1
[58] Field of Search ................................. 606/1, 45, 46, 606/48–52, 142, 143, 205–207, 169; 604/21, 22; 227/175.1, 180.1, 901; 601/2

[56] References Cited

U.S. PATENT DOCUMENTS

| | | |
|---|---|---|
| 2,714,890 | 8/1955 | Vang . |
| 2,845,072 | 7/1958 | Shafer . |
| 3,053,124 | 9/1962 | Balamuth et al. . |
| 3,086,288 | 4/1963 | Balamuth et al. . |
| 3,526,219 | 9/1970 | Balamuth . |
| 3,636,943 | 1/1972 | Balamuth . |
| 3,657,056 | 4/1972 | Winston et al. . |
| 3,862,630 | 1/1975 | Balamuth . |
| 3,898,992 | 8/1975 | Balamuth . |
| 4,375,961 | 3/1983 | Brooks . |
| 4,674,498 | 6/1987 | Stasz . |
| 4,723,545 | 2/1988 | Nixon et al. . |
| 4,872,456 | 10/1989 | Hasson . |
| 5,105,025 | 4/1992 | Main et al. . |
| 5,176,677 | 1/1993 | Wuchinich ................................ 604/22 |
| 5,176,688 | 1/1993 | Narayan et al. ......................... 606/128 |
| 5,190,541 | 3/1993 | Abele et al. ............................... 606/46 |
| 5,322,055 | 6/1994 | Davison et al. ........................... 604/22 |
| 5,324,299 | 6/1994 | Davison et al. . |
| 5,344,420 | 9/1994 | Hilal et al. . |
| 5,389,098 | 2/1995 | Tsuruta et al. ........................... 606/142 |
| 5,403,312 | 4/1995 | Yates et al. ................................ 606/49 |
| 5,405,344 | 4/1995 | Williamson et al. .................... 606/143 |
| 5,445,638 | 8/1995 | Rydell et al. .............................. 606/51 |
| 5,458,598 | 10/1995 | Feinberg et al. .......................... 606/51 |
| 5,562,700 | 10/1996 | Huitema et al. ......................... 606/207 |
| 5,578,031 | 11/1996 | Wilk et al. ............................... 606/49 |

FOREIGN PATENT DOCUMENTS

| | | |
|---|---|---|
| 1-232948 | 9/1989 | Japan . |
| WO 93/08754 | 5/1993 | WIPO . |

*Primary Examiner*—Michael Peffley
*Attorney, Agent, or Firm*—Bernard E. Shay

[57] ABSTRACT

A therapeutic ultrasonic instrument is provided for hemostatic cutting and/or cauterizing of tissue. A preferred embodiment provides an end effector which grasps tissue while a cutting element energized by ultrasonic energy is passed through the tissue to cut and cauterize the tissue while it is being held by the tissue grasping portion of the end effector. One embodiment further includes staples which are applied to the tissue as well.

10 Claims, 10 Drawing Sheets

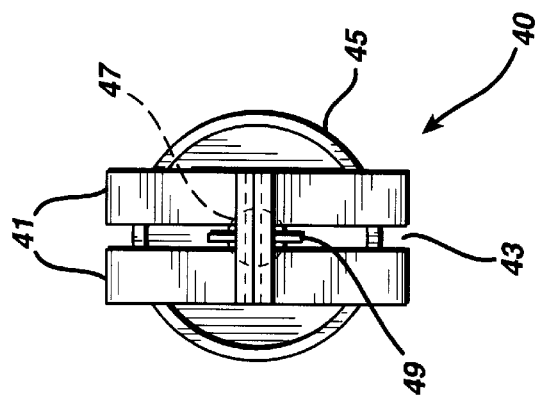
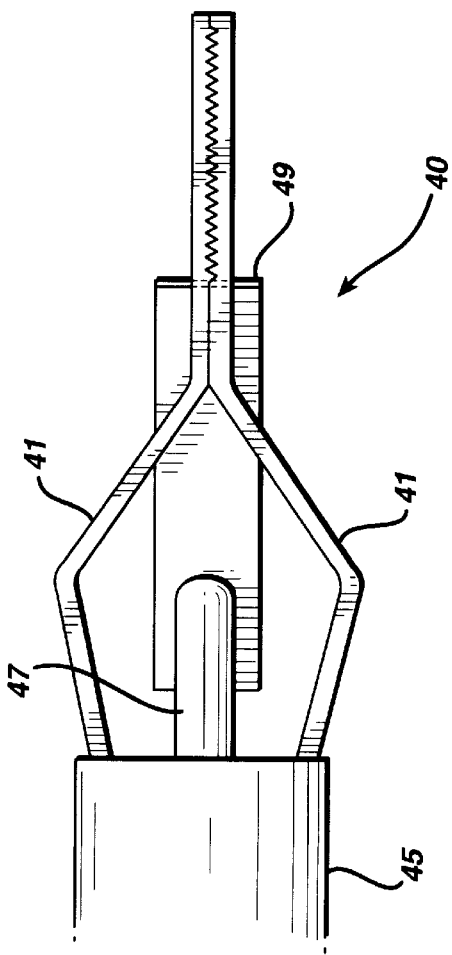
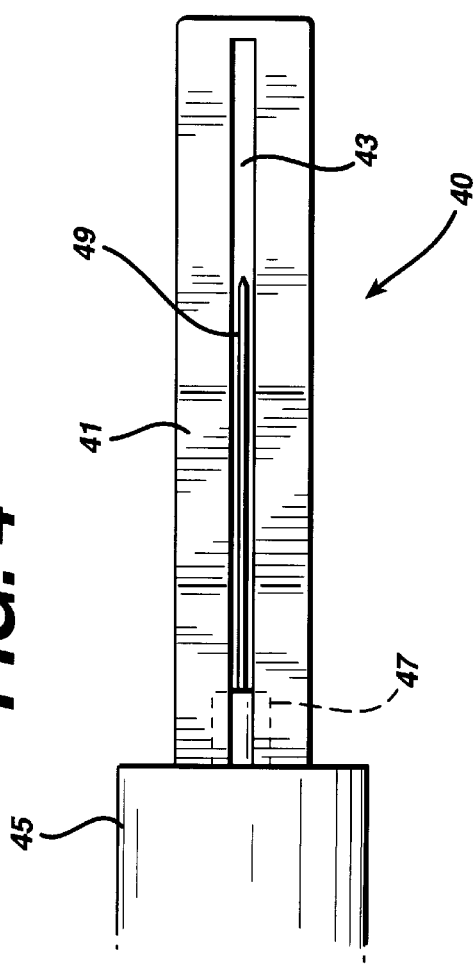

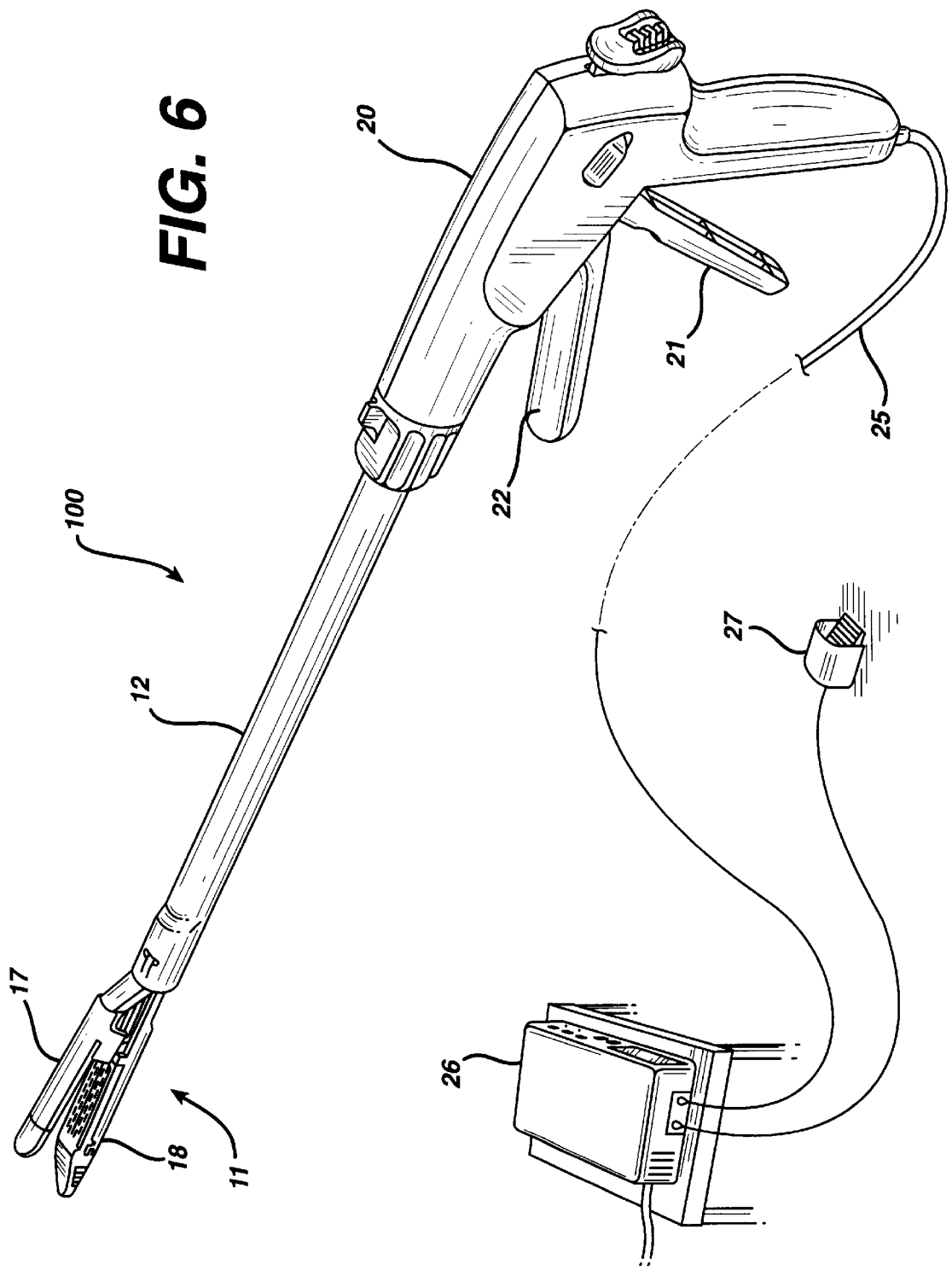

ULTRASONIC HEMOSTATIC AND CUTTING INSTRUMENT

This is a continuation, of application Ser. No. 08/284,338, filed Aug. 2, 1994 now abandoned.

FIELD OF THE INVENTION

This invention relates to a therapeutic ultrasonic instrument for cutting, cauterization, coagulation and/or tissue welding in the performance of surgical procedures, especially endoscopic procedures.

BACKGROUND OF THE INVENTION

Surgical procedures frequently require cutting of tissue causing bleeding at the site of the cutting. Thus hemostasis is important in surgical procedures. Hemostasis is even more crucial in endoscopic or laparoscopic surgery where if the bleeding is not kept under control, the laparoscopy must be abandoned and the patient's body cut to perform open surgery so that inaccessible bleeding may be controlled.

Various techniques have been adopted to control bleeding with varying degrees of success, such as, for example, suturing, applying clips to blood vessels, stapling, as well as tissue heating, laser, electrocautery and ultrasonic techniques.

Surgical staplers have been used for tissue joining and to provide hemostasis in conjunction with tissue cutting. Such devices include, for example, linear and circular cutting and stapling instruments. Typically, a linear cutter has parallel rows of staples aligned in a cartridge with a slot through which a cutting means may pass between the rows of staples. This type of surgical stapler secures the tissue for improved cutting, joins layers of tissue, and provides hemostasis by applying parallel rows of staples to layers of surrounding tissue, as a cutting means cuts between parallel rows. These types of cutting and stapling devices have been used successfully in procedures involved in fleshy tissue such as, muscle or bowel, particularly in bowel resection procedures. Similarly, circular cutting and stapling devices have successfully been used, for example, in anastomotic procedures where a lumen is rejoined.

However, improvements are desirable with such cutting and stapling devices to optimize the hemostasis, particularly where the procedure involves cutting highly vascularized tissue, such as mesentery or adnexa, which is prone to having hemostasis problems.

Ultrasonically energized surgical instruments have been used to cut and simultaneously coagulate or cauterize tissue. Typically, such devices include a knife blade at the end of the instrument which receives and transmits ultrasonic energy at a therapeutic amplitude and frequency. Such devices may be used to cut and/or to cauterize tissue. However, these devices are sometimes difficult to use to manipulate tissue and achieve the desired cutting and/or coagulating effect.

SUMMARY OF THE INVENTION

It is therefore an object of the present invention to provide a therapeutic ultrasonic cutting and hemostatic instrument which is capable of holding or grasping tissue as it is cut and/or cauterized by an ultrasonic cutting element.

It is a further object of the invention to provide an ultrasonic cutting and stapling device adapted to cauterize and cut tissue along a cutting path generally adjacent a line of placed staples.

It is yet another object of the invention to provide a linear cutting and stapling device with parallel rows of staples between which an ultrasonic knife blade is used to cut and coagulate blood vessels.

It is yet another object of the invention to provide a circular cutting and stapling device with a circular ultrasonic cutting element or blade for cutting and coagulating tissue in a cutting path adjacent placed staples.

These and other objects of the invention are illustrated in a surgical instrument including an end effector capable of engaging tissue and an ultrasonic cutting and coagulating element associated with the end effector for cutting and cauterizing tissue engaged by the end effector.

Preferably the end effector is comprised of a first and second element pivotally or otherwise movable with respect to each other to engage tissue therebetween.

In one embodiment the first and second elements close together to engage tissue. An ultrasonically vibrating cutting element associated with the end effector is then passed through the engaged tissue to cut and cauterize the tissue. In a variation of this embodiment, the first and second elements close together to engage tissue. An ultrasonic cutting blade extends from either the first or second elements, and is in contact with the tissue when the elements are closed together. When it has been determined that the tissue is appropriately situated between elements, the cutting blade is energized. The blade, which in this particular embodiment is preferably dull, acts as a cutting element when ultrasonically vibrated to cut the engaged tissue.

In another embodiment, the first and second elements engage tissue and apply staples either prior to or as the ultrasonic cutting element is passed through a slot extending longitudinally through first and second elements. Thus the cut is made adjacent the staple line. For example, a linear cutting instrument with an ultrasonically energized blade may be used. In such instrument, one or more rows of staples is applied on each side of a cutting path defined as an ultrasonically energized blade is passed between the row of staples through a slot in the end effector. Or, for example, a circular stapling instrument may include an ultrasonically energized blade. In such instrument, staples are used to connect two lumens of tissue and a circular cutting element vibrating at an ultrasonic frequency, cuts the tissue adjacent the staples to open the lumen while providing hemostasis through tissue cauterization.

The mechanical cutting action of the knife blade may be controlled either mechanically or through other control mechanisms. For example an electronic instrument control may be used to control the rate of cutting element movement to insure that the knife is in contact with the tissue for a sufficient amount of time to enable cauterization.

Another embodiment provides a means for detecting an abnormal load which is out of a predetermined range. This feature may be used for detecting instrument abnormalities, as well as to provide feedback to the user as to the status of the tissue that is being treated.

In one embodiment, the feedback mechanism may comprise an acoustical impedance feedback system in which a light sensor located on an inactive portion of the instrument is used to detect light emitted from a light source and reflected from an active portion, i.e., an ultrasonically vibrating portion of the instrument, to determine the load or impeding effect of tissue on the cutting element.

In another embodiment the feedback mechanism may comprise a passive piezoelectric element located within a piezoelectric stack of an ultrasonic transducer. The passive element vibrates with the other piezoelectric ceramic elements of the stack, but unlike the other elements, is not energized. The vibration of the passive element creates an oscillating voltage across the element which corresponds to the vibrations of the piezoelectric stack. From the voltage across the element the load on the cutting element can be determined by methods well-known in the art. The passive element may be coupled to a control means of a generator used to supply electrical energy to the ultrasonic transducer to cause vibrations.

Other feedback systems may also be used, for example, a pressure detector or strain gauge may be used to detect tissue presence, status or type. Electrical parameters may be used to sense and determine the variation in load conditions on the cutting element as acoustical impedance is related to the system impedance of the generator and instrument. In such a system, either phase differences of voltage and current or magnitude ratios of voltage and current supplied to the transducer, are used to make this determination.

These and other objects of the invention will be better understood from the following attached detailed description of the drawings when taken in conjunction with the Detailed Description of the Invention.

DETAILED DESCRIPTION OF THE DRAWINGS

FIG. 3 illustrates a side view of the distal end of the end effector of the instrument in FIG. 1;

FIG. 4 illustrates a top view of the distal end of the end effector of the instrument in FIG. 1;

FIG. 5 illustrates a front view of the distal end of the end effector of the instrument in FIG. 1;

FIG. 6 is a perspective view of an endoscopic ultrasonic linear stapling and cutting instrument of a first embodiment of the present invention;

DETAILED DESCRIPTION OF THE PREFERRED EMBODIMENTS

Figure 1:
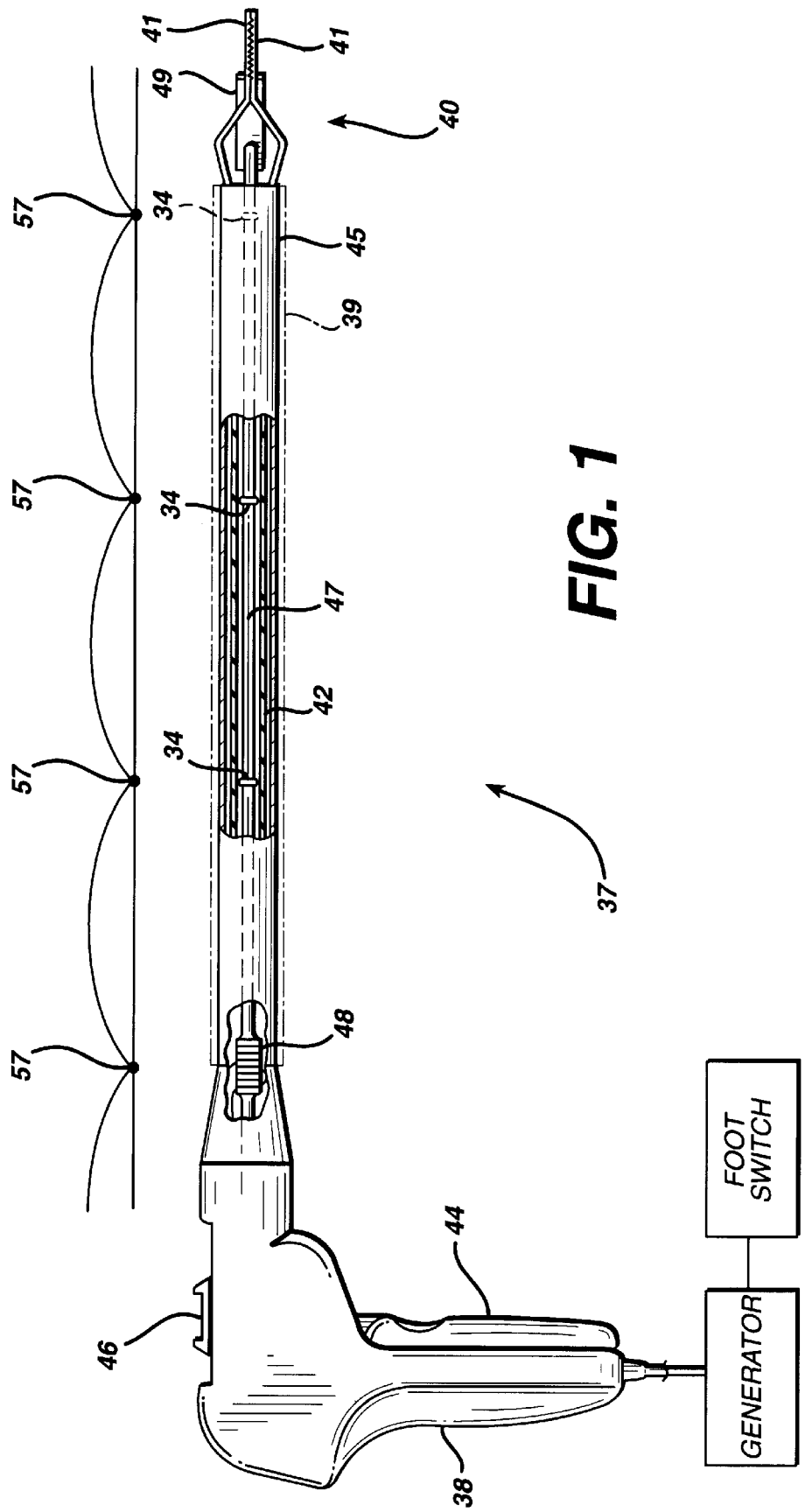
FIG. 1 illustrates a side view of an ultrasonic hemostatic cutting instrument of the present invention.

Referring now to FIGS. 1–5 there is illustrated a first embodiment of a hemostatic cutter 37 of the present invention. The cutter comprises a handle 38, coupled to an outer tube 39 and an end effector 40 extending from the distal end of the outer tube 39. The end effector 40 includes two jaw members 41 adapted to close together to engage, grasp or hold tissue between the jaw members 41. A slot 43 extends longitudinally through the jaws to receive a cutting element 49 associated with the end effector.

The handle 38 includes a closure trigger 44 coupled to an inner tube 45 extending through the outer tube 39. When actuated, the closure trigger 44 moves the inner tube 45 longitudinally over a ramped portion of the jaw members 41 to close the jaw members 41 together.

The handle 38 also includes cutting actuation button 46 which is couple to a shaft 47 extending through inner tube 45. The shaft 47 includes an ultrasonic piezo electric stack 48 adapted to propagate ultrasonic vibrations along the shaft 47 when the stack 48 is provided with electrical energy. A cutting element 49 is coupled to the distal end of the shaft 47.

An insulation 42 extends substantially along the length of the shaft 47 and is separated from the shaft 47 by O-rings 34 at nodal points along the length of the insulation 42. The cutting element 49 ends at an anti node.

In operation, the jaw members 41 are placed around tissue to be treated. The closure trigger 44 is actuated to move the inner tube 45 distally over a ramped portion of the jaw members 41 to close the jaw members 41 over the tissue.

Energy is supplied to the ultrasonic stack 48 in a manner similar to the device illustrated in FIGS. 6–11 as described in more detail below, i.e., by deliver of electrical energy through wires from a generator to the ultrasonic stack 48. The user then advances the cutting actuation button 46 which thereby distally advances the shaft 47 and advances the ultrasonically vibrating cutting element 49 through the slot 43 and through the grasped tissue, cutting and simultaneously cauterizing the tissue.

Referring now to FIGS. 6–10 there is illustrated another embodiment of the present invention. A linear cutting and stapling instrument 100 is shown having an actuation end or housing 20 coupled to an outer tube 12 out of which an end effector 11 extends. The end effector 11 has first and second tissue engaging elements 17, 18 which are pivotally connected to one another so that the first and second elements 17, 18 are capable of opening to capture tissue and closing towards each other to engage tissue between the elements 17, 18. The opening and closing of the two elements is actuated by closure trigger 21 on housing 20 which advances the outer tube 12 over the proximal ends of elements 17, 18.

An ultrasonic transducer which is comprised of a piezoelectric stack 23 is contained within housing 20. The piezoelectric stack is comprised of piezoelectric ceramic transducer elements alternatively energized by positive and ground electrodes (not shown). The stack 23 is coupled to a shaft 14 which extends through the outer tube 12 and ends in a cutting element 28. The stack 23 includes an amplifier 24 on its distal end with transitions into a shaft 14. The shaft 14 and amplifier 24 are preferably constructed of a material which efficiently conducts ultrasonic energy such as an alloy of titanium or aluminum. The amplifier 24 amplifies ultrasonic waves which are then transmitted through down the shaft 14 to the cutting element 28.

The shaft 14 includes insulation 15 surrounding the outer diameter of the shaft 14. The insulation 15 is preferably constructed of a material which has a low thermal and electrical conductivity and a low coefficient of friction such as teflon or poly carbonate. The shaft 14 is isolated from the insulation 15 at nodal points 16 by O-rings 29. The O-rings 29 preferably comprise non-ultrasonic energy conductive material such as a plastic. Nodal points 16 are the points at which the sine of the ultrasonic vibration amplitude is equal to zero, i.e., where the ultrasonic vibration energy is minimized.

Figure 2:
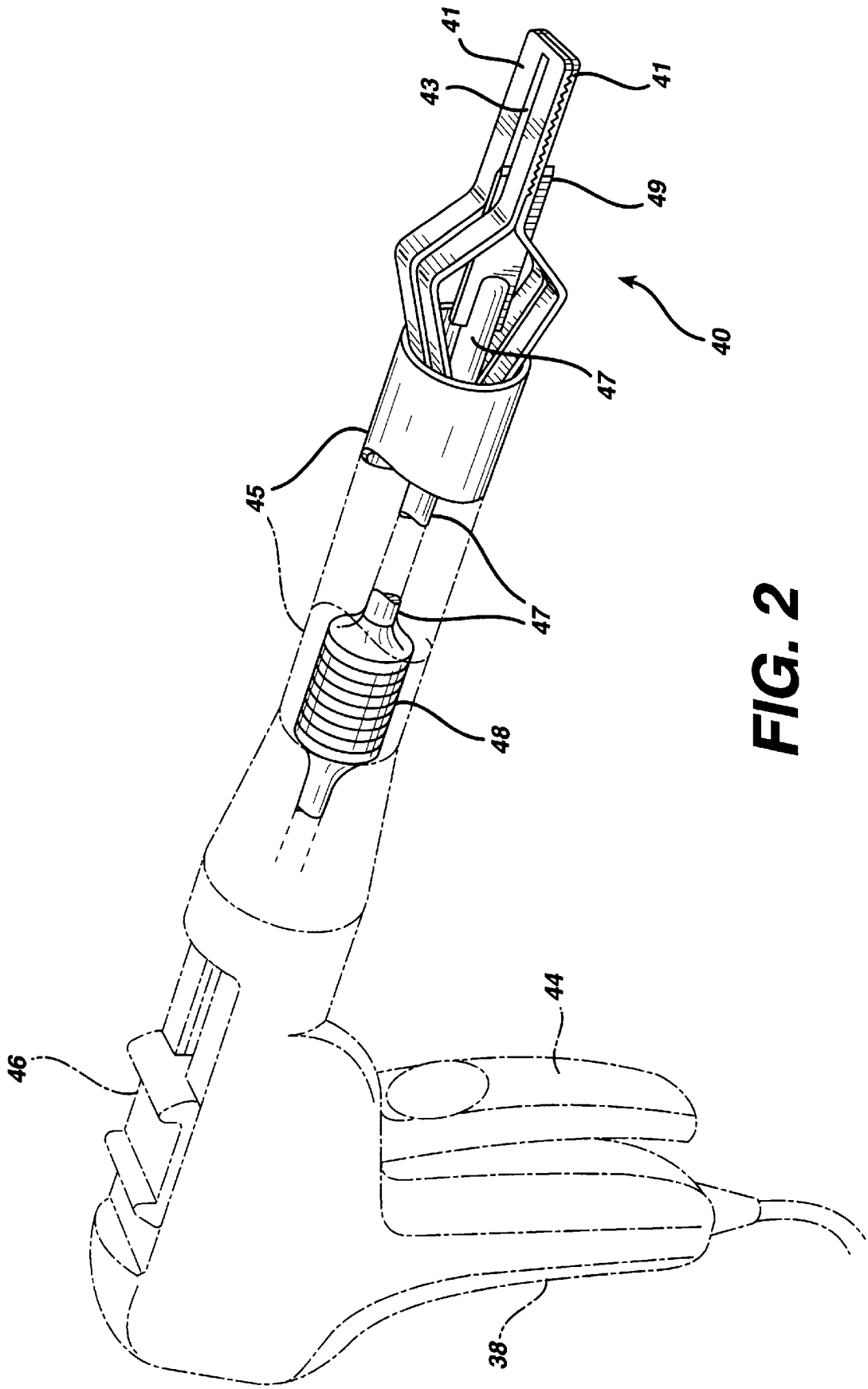
FIG. 2 illustrates a break away perspective view of the instrument of FIG. 1.
Figure 7:
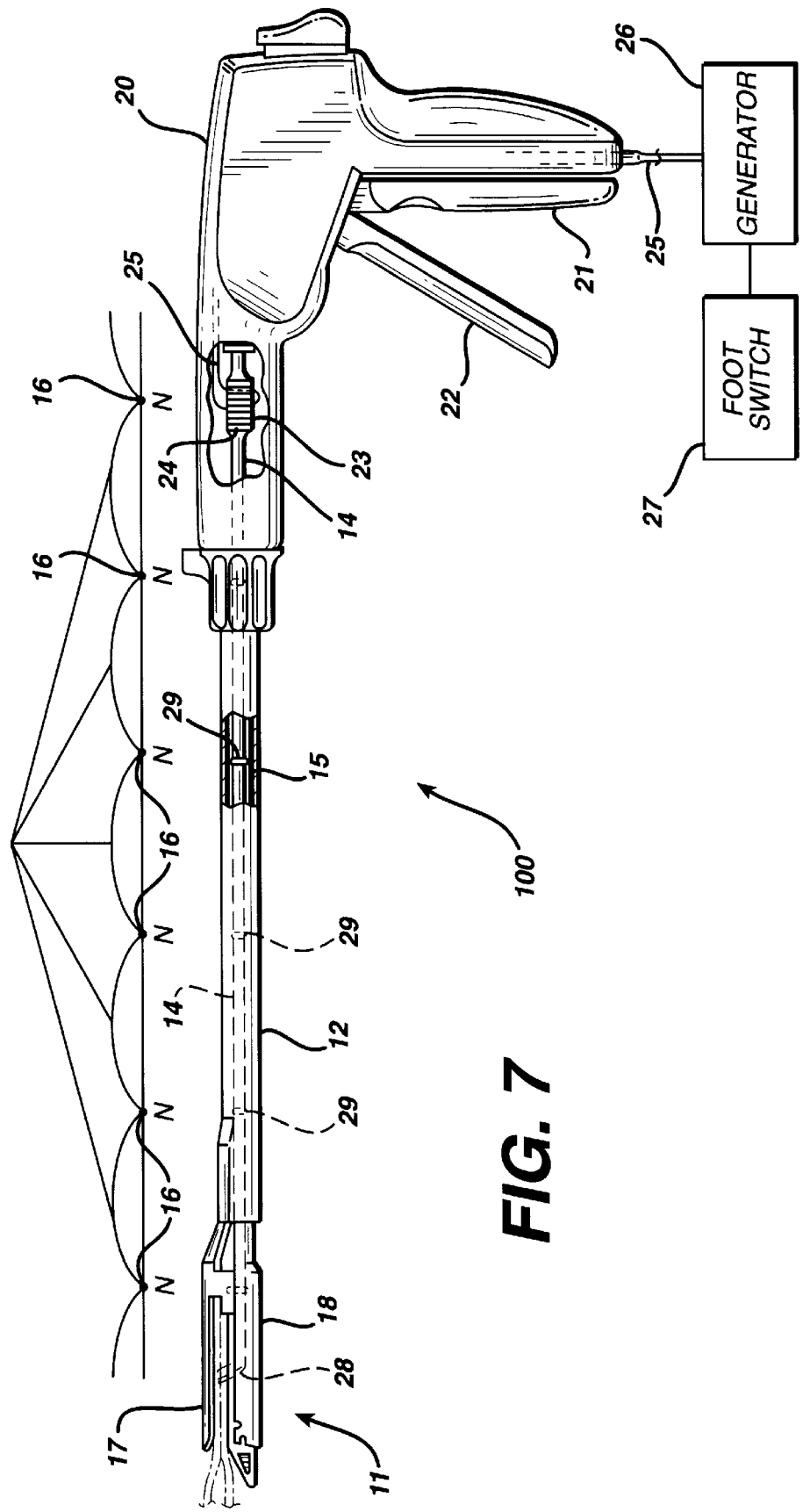
FIG. 7 is a side cross-sectional view of the instrument of FIG. 6.
Figure 8:
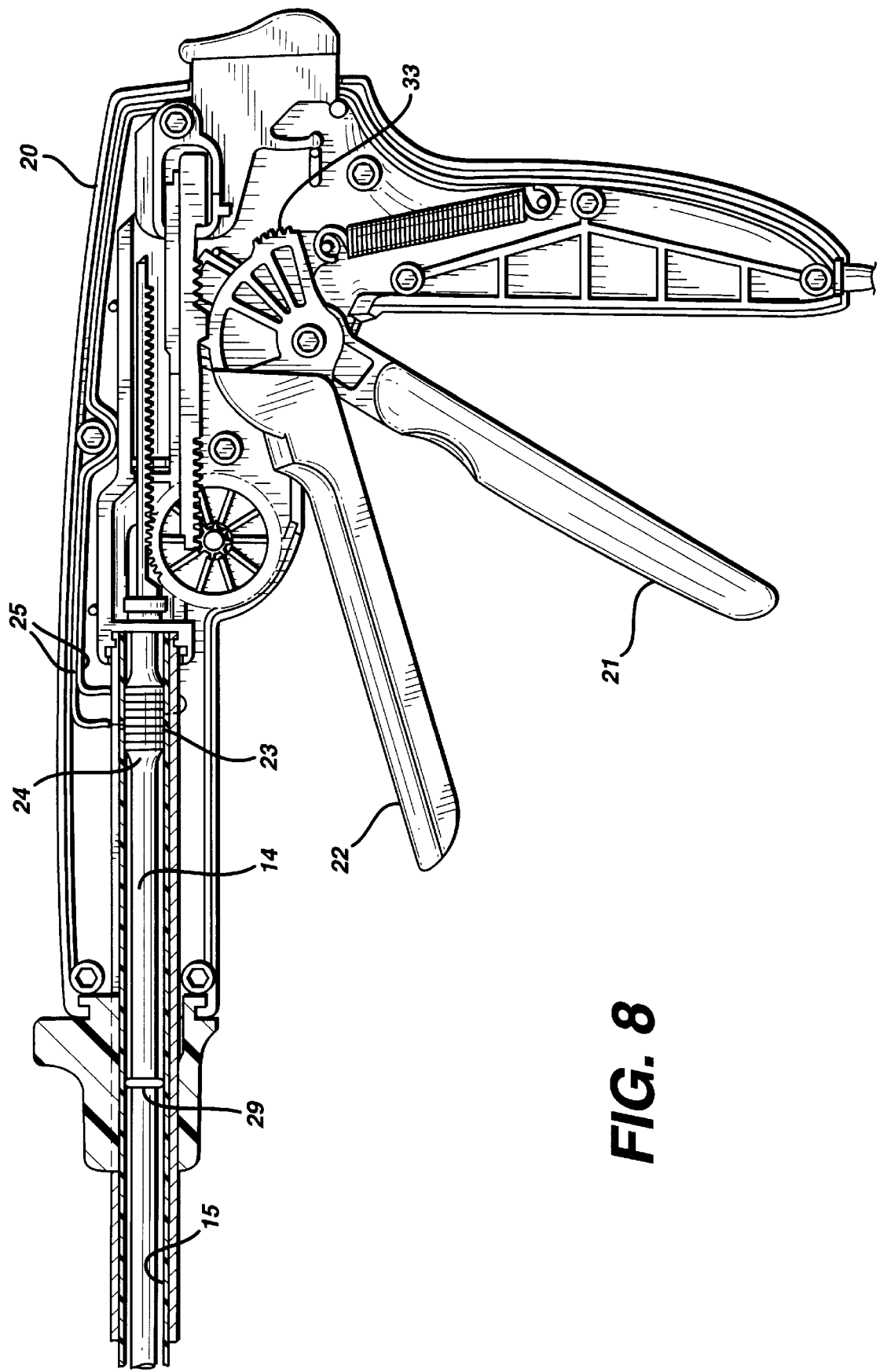
FIG. 8 is an enlarged side cross-sectional view of the instrument housing of the instrument of FIG. 7.
Figure 9:
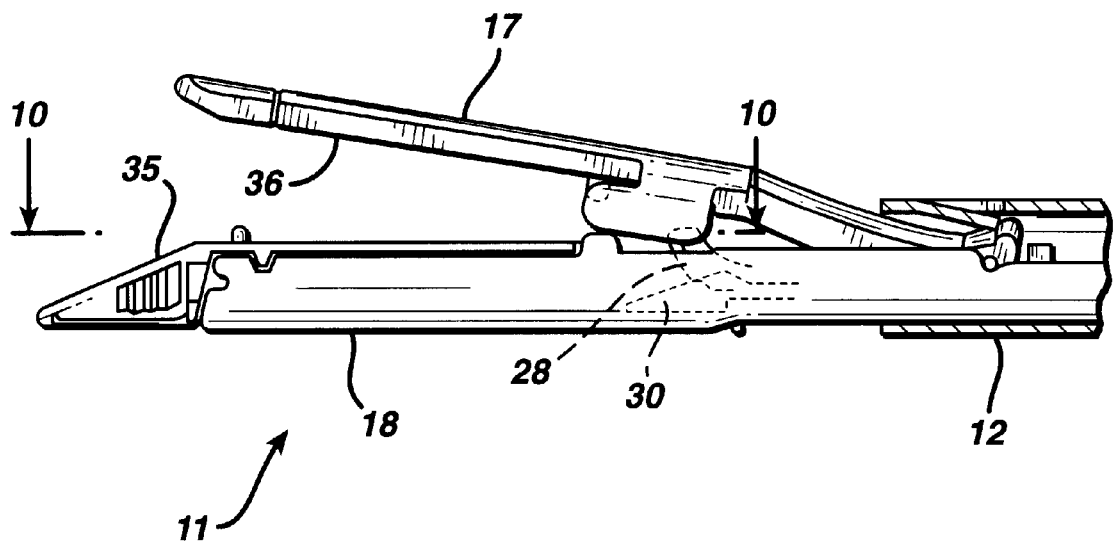
FIG. 9 is an enlarged cross-sectional view of the end effector of the instrument illustrated in FIG. 7.
Figure 10:
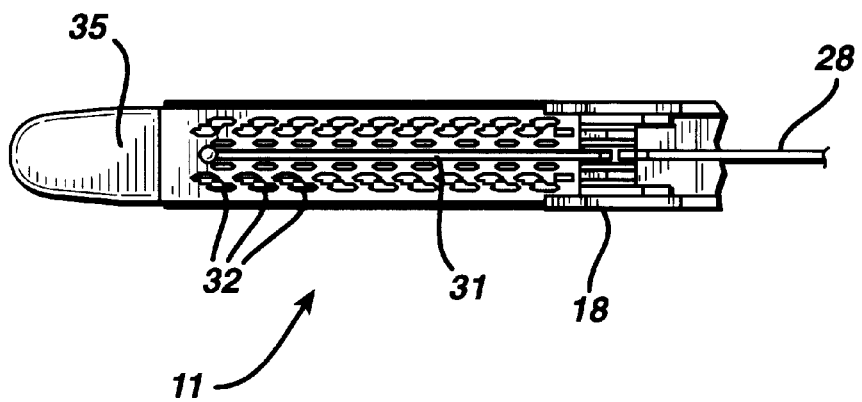
FIG. 10 is a top view of the second tissue engaging element of the end effector of the instrument of FIG. 6.

Voltage supply wires 25 representing positive and ground electrodes, enter through the handle and are coupled to the ultrasonic stack 23. The wires 25 are electrically isolated from each other, a first wire coupled to a positive electrode of the stack and the second wire coupled to the ground electrode. The wires 25 lead to a generator 26, external to the instrument 100 as schematically illustrated in FIG. 2. When energy is supplied via the generator 26 to the stack 23, the stack 23 vibrates at a predetermined ultrasonic frequency. The stack 23 thus acts as an ultrasonic transducer. Other ultrasonic transducers, for example, a magneto-restrictive element, alternatively may be used.

The nodal points 16 are spaced at equal distances from an adjacent nodal point. The piezoelectric stack 23 itself is centered on nodal point 16.

The nodal points 16 are at a distance along the shaft equal to an integer multiple of ½ wavelength of a predetermined ultrasonic frequency. A footswitch 27, also schematically illustrated, is connected to the generator and may be used to switch on and off the electrical energy supply to the ultrasonic stack 23.

The stack 23 and the shaft 14 are longitudinally movable in distal and proximal directions through the outer tube 12. A firing trigger 22 is used to fire the staples 32 and advance the cutting element 28, after the closure trigger 21 has been actuated to engage tissue between the elements 17, 18. The firing trigger 22 advances the gear 33 which translates a user force applied to the firing trigger 22 into longitudinal movement of the stack 23, shaft 14 and cutting element 28.

When the firing trigger 22 is actuated, the cutting element 28 moves within a slot 31 extending longitudinally through first and second elements 17, 18. Also coupled at the distal end of the shaft are drivers 30 for driving staples through engaged tissue. The drivers 30 move within the second element 18 simultaneously with the movement of the cutting element 28. The second element 18 includes a cartridge 35 containing staples 32 arranged in parallel rows on each side of slot 31 while the first element 17 comprises an anvil 36 for closing the staples 32.

Ultrasonic energy is transmitted from the stack 23 along the shaft 14 into the cutting element 28 which transmits the energy to the tissue engaged by the elements 17, 18. As the shaft 14 is moved distally, an ultrasonically vibrating cutting element 28 cuts and cauterizes the tissue engaged by the first and second element 17, 18, while the drivers 30 fire staples simultaneously on each side of the cut line. The ultrasonic energy causes cutting or dissection of the tissue as well as cauterization. It is believed that when the tissue has cauterized to a desirable degree, the tissue will decouple from the cutting element which is initially in contact with the tissue. The user or a control mechanism controls the speed of cutting element 28 actuation so that cutting element 28 will have sufficient contact time with the tissue in order to cauterize the tissue to a desired degree.

Referring now to FIGS. 11–15 there is illustrated another embodiment of the present invention. A circular stapling instrument 50 is shown having a housing portion 51 including a firing trigger 53 and a closure knob 52; a hollow outer tube 54 coupled to the housing 51; and an end effector 58 coupled to the distal end of the outer tube 54.

The closure knob 52 is rotatable with respect to the handle 51 and is coupled to a closure shaft 69 extending longitudinally through the outer tube 54 to the end effector 58. The firing trigger 53 is adapted to move an actuation shaft 76 longitudinally through the outer tube 54. In this embodiment the shaft 76 is hollow with the closure shaft 69 extending longitudinally through the shaft 76 and appropriately insulated from the shaft 76 by the O-ring 77 at nodal points 57. These O-rings 77 also separate insulation 56 surrounding the outer diameter of the shaft 76 from the shaft. An alternative embodiment may include a solid shaft for delivering ultrasonic vibrations to a cutting element, where the closure shaft is a hollow tube surrounding the outer diameter of the shaft.

The end effector 58 comprises a first element 59 and a second element 60. The first element 59 includes a first tissue engaging surface 70 and a opening 71. A cutting element 55 is contained in said first element 59 and is adapted to extend from the distal end of said first element 59 through the opening 71. The second element 60 extends distally of the first element 59 and includes a second tissue engaging surface 72 on its proximal end. The second tissue engaging surface 72 includes an anvil 73 for receiving staples 62 driven from first element 59 through tissue engaged by first and second elements 59, 60.

Figure 11:
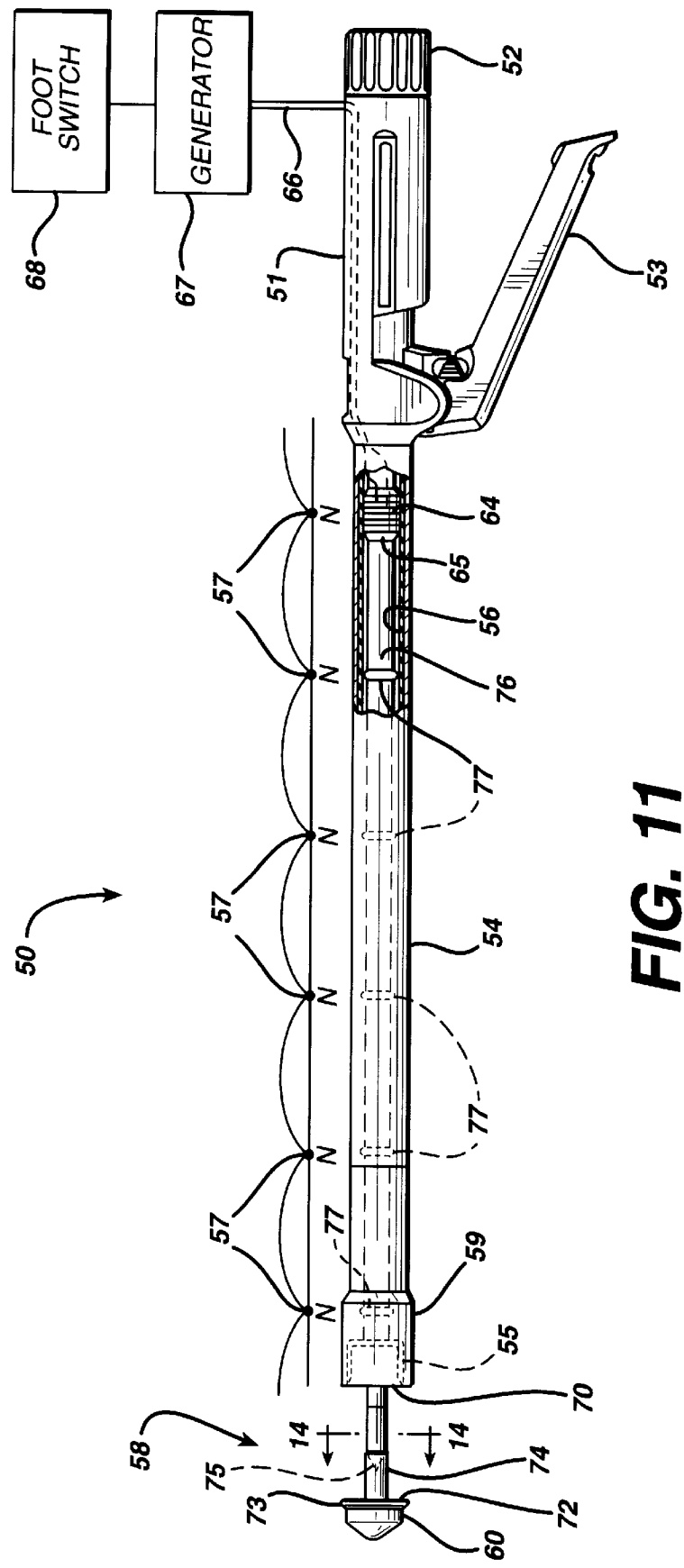
FIG. 11 is a side partial cut away view of a circular cutting instrument of a second embodiment of the present invention.
Figure 12:
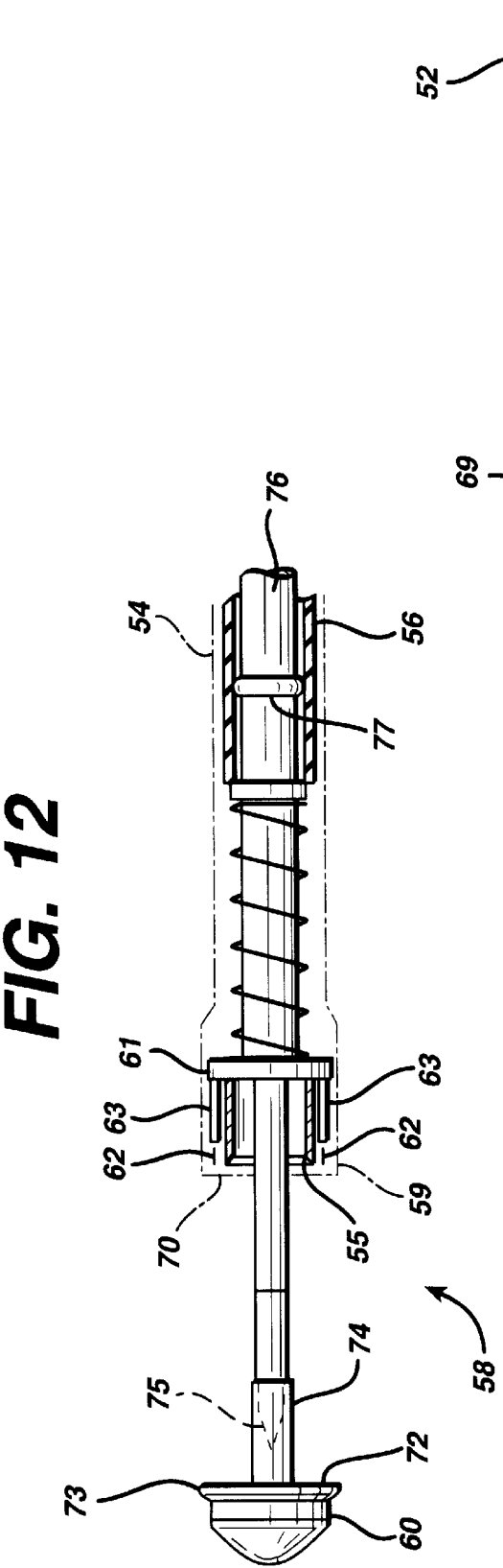
FIG. 12 is an enlarged cross-sectional view of the end effector of the instrument illustrated in FIG. 11.
Figure 13:
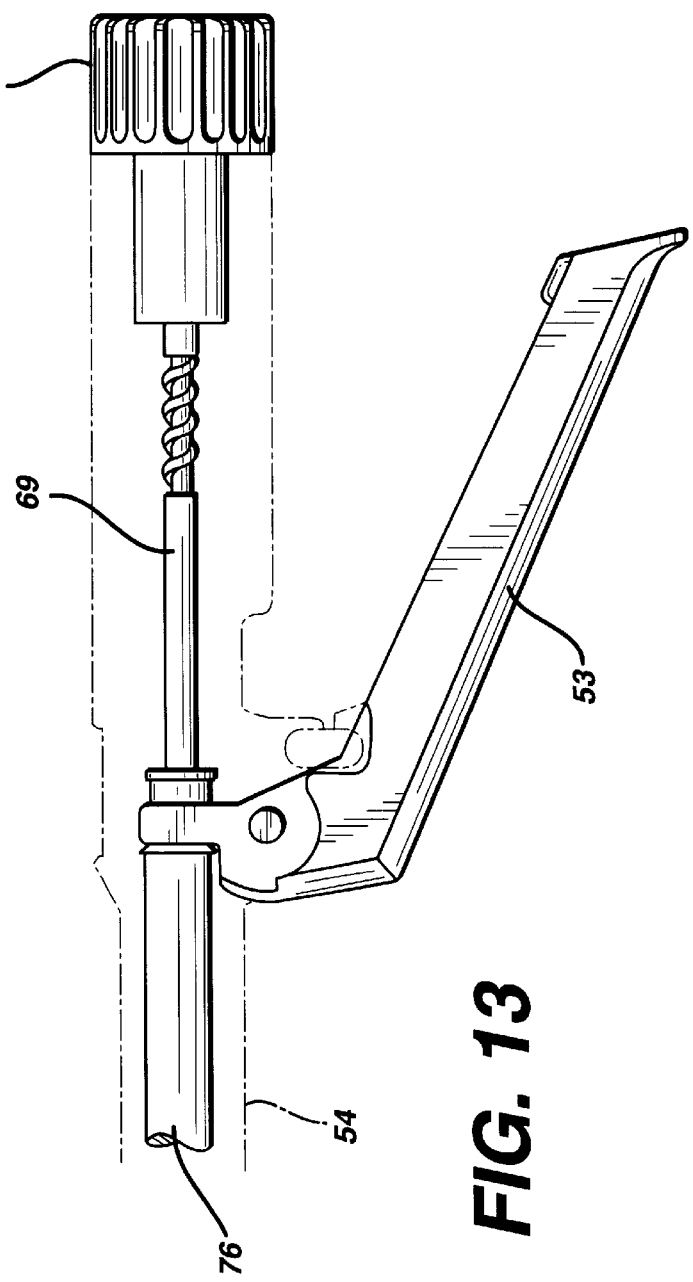
FIG. 13 is an enlarged cross-sectional view of the handle of the instrument illustrated in FIG. 11.
Figure 14:
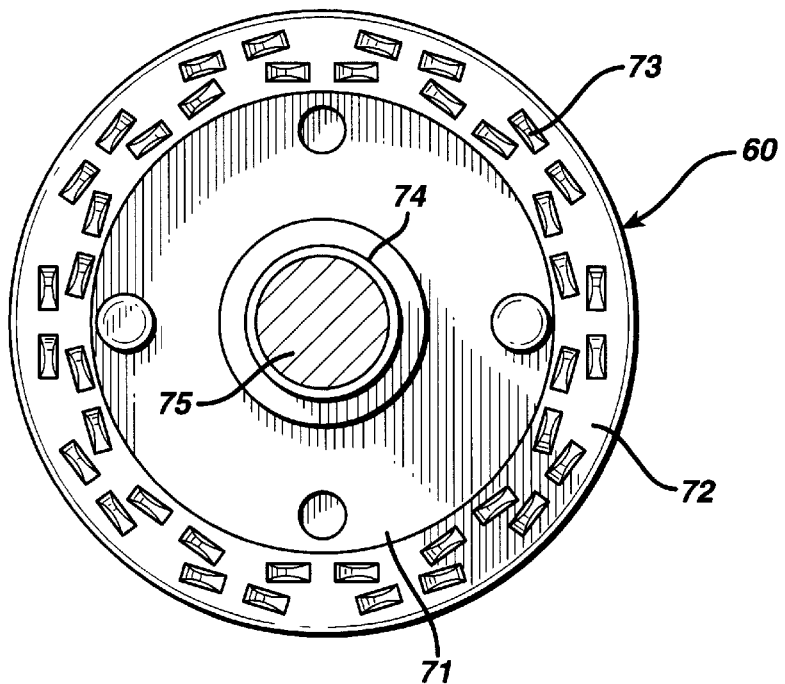
FIG. 14 is a front end view of the cutting portion of the end effector of the instrument in FIG. 11 along the lines 14—14.
Figure 15:
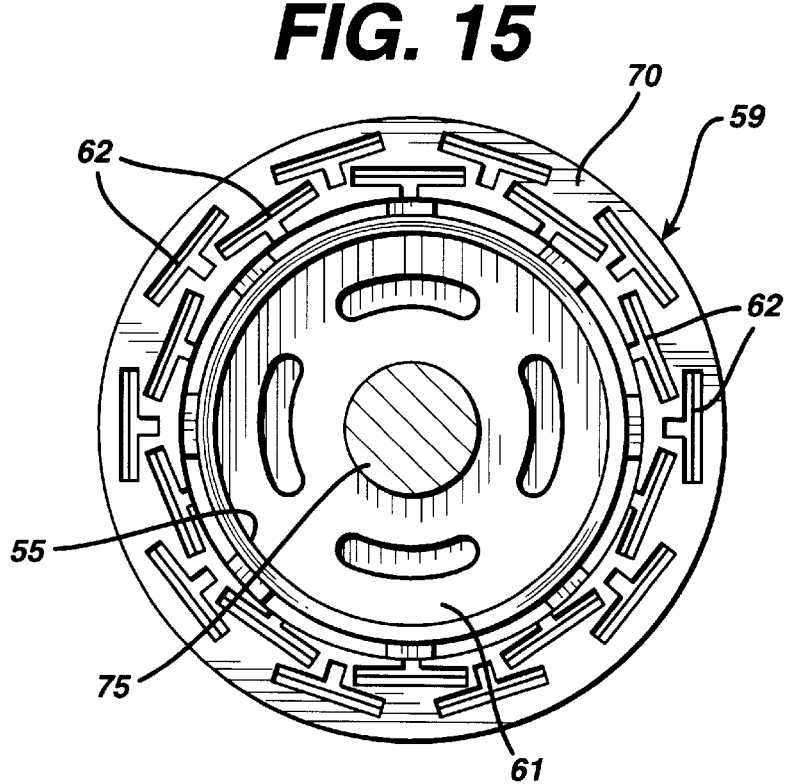
FIG. 15 illustrates a back end view of the anvil portion of the end effector of the instrument in FIG. 11.

The cutting element 55 includes towards its proximal end, an ultrasonic piezoelectric stack 64 for generating ultrasonic vibrations. A pair of wires 66 are in electrical communication with the stack 64. The wires 66 extend out of the handle 51 and are in communication with a generator 67, schematically illustrated in FIG. 11. A generator 67 supplies electrical energy through wires 66 to ultrasonic piezoelectric stack 64 to cause the stack to vibrate at a predetermined ultrasonic frequency. A footswitch 68, also schematically illustrated in FIG. 11, is coupled to the generator 67. The footswitch 68 may be used to switch on and off the generator 67.

In use, the first and second elements 59, 60 are separated from each other. Tissue forming a first lumen is engaged by the first element 59. Typically the first lumen has been closed by a purse string type suture around a connector pin 75 extending distally from the first element 59. The first lumen is to be rejoined by tissue forming a second lumen. The second lumen is engaged by the second element 60. The second lumen is closed by a purse string type suture around a shaft connector 74 extending proximally from the second element 60. The closure shaft 69 ends in a connector pin 75 which extends distally from the first element 59. The connector pin 75 is inserted and locked into the shaft connector 74 adapted to receive the connector pin 75. The second element 60 is then moved towards the first element 59 in a proximal direction by the rotation of closure knob 52 which in turn rotates and retracts the closure shaft 69. The closure shaft 69 extends through the outer tube 54 and is rotatable coupled to the second element 60. The rotation of the closure shaft 69 brings the tissue lumen engaged by the first element 59 adjacent to the lumen tissue engaged by the second element 60. When this has occurred the instrument is ready to be fired.

The firing of the instrument is actuated by the firing trigger 53 which moves the shaft 76, and thus the cutting element 55, in a proximal direction. At the same time the firing trigger 53 moves the driver base 61 distally. The driver base 61 in turn advances the driver 63 to drive the staples 62 from the first element 59 through the tissue and into the anvil 73 of the second element 60. Thus, the tissue is joined by the staples and at the same time the cutting element cuts excess tissue from the first and second tissue lumens blocking the newly formed lumen. The circular cutter is operated in a manner similar to that of mechanical circular cutters known in the art. An example of such device is described, for example, in U.S. Pat. No. 5,104,025 incorporated herein by reference.

The ultrasonic stack 64 is centered on a nodal point 57 on the cutting element 55. The cutting element 55 is surrounded by insulation 56 which only contacts the cutting element 55 at nodal points 57.

As the instrument is being fired, the footswitch 68 is also used to activate the generator 67 to supply electrical energy to the ultrasonic stack 64. The stack 64 vibrates at a predetermined ultrasonic frequency. The ultrasonic vibrations are propagated down the shaft 76 to the cutting element 55. When the firing trigger 53 is actuated, the cutting element 55 extends from the distal end of the second element to cut the tissue as described above. If the footswitch is activated, ultrasonic energy is transmitted down the cutting element 55 to the distal end of the cutting element 55. The ultrasonic energy may provide both cutting energy and cauterization energy to the tissue being cut.

Several variations of this inventions have been described in connection with two specific embodiments involving endoscopic cutting and stapling. Naturally, the invention may be used in numerous applications where hemostasis is desired. For example, these devices may be used with or without staples. Other instruments with ultrasonic energized tissue grasping cutting and/or cauterizing elements are intended to be within the scope of the invention. Accordingly, it will be understood by those skilled in the art that various changes and modifications may be made in the invention without departing from its scope which is defined by the following claims and their equivalents.

We claim:

1. A surgical instrument comprising:
    an end effector including first and second elements, wherein at least one of said first and second elements is moveable with respect to the other element to engage tissue therebetween;
    a cutting element adapted to extend from said first element to contact tissue engaged by said first and second elements;
    an ultrasonically energized blade disposed at a distal end of said cutting element wherein said blade is moveable in a direction which is substantially parallel to a central axis of said shaft;
    a shaft coupled to said cutting element;
    an ultrasonic transducer coupled to said shaft, said transducer adapted to propagate ultrasonic vibrations along said shaft to said cutting element to cause said cutting element to cut and/or cauterize tissue, wherein said shaft and said transducer are moveable in a direction which is substantially parallel to a central axis of said shaft such that movement of said transducer and said shaft bring said ultrasonically energized blade into contact with tissue engaged by said first and second elements; and
    an electrical energy communication means for delivering electrical energy to said transducer to cause said transducer to vibrate ultrasonically.

2. A surgical instrument comprising:
    a handle;
    a hollow tube coupled to said handle;
    an end effector extending distally from said tube, said end effector comprising first and second elements;
    an actuating element operatively coupled to at least one of said first and second elements, said actuating element arranged to move said at least one element towards the other said element to engage tissue therebetween;
    an opening extending longitudinally through said first element;
    a shaft extending through said hollow tube;
    a cutting element coupled to said shaft, said cutting element adapted to extend from said first element through said opening to cut and/or cauterize tissue between said first and second elements;
    an ultrasonically energized blade disposed at a distal end of said cutting element wherein said blade is moveable in a direction which is substantially parallel to a central axis of said shaft; and
    an ultrasonic transducer operatively coupled to said cutting element to transmit ultrasonic vibrations to said cutting element, wherein said shaft and said transducer are moveable in a direction which is substantially parallel to a central axis of said shaft such that movement of said transducer and said shaft bring said ultrasonically energized blade into contact with said tissue engaged by said first and second elements.

3. The surgical instrument of claim 2 wherein said first element comprises a staple cartridge containing staples;
    wherein said second element comprises an anvil adapted to receive and close staples driven from said cartridge through tissue engaged by said first and second elements;
    wherein said first element is adapted to engage a first lumen and said second element is adapted to engage a second lumen;
    wherein said staples are arranged to join the first lumen to the second lumen; and
    wherein said cutting element is approximately circular in shape.

4. A surgical instrument comprising:
    an outer tube with a lumen extending therethrough, said outer tube having a distal end;
    an end effector coupled to said distal end of said outer tube, said end effector including first and second elements,
    an actuating element operatively coupled to at least one of said first and second elements, said actuating element arranged to move said at least one element towards the other said element to engage tissue between said first and second elements;
    a shaft having a distal end said shaft extending through said lumen of said outer tube;
    a cutting element coupled to said distal end of said shaft, said cutting element arranged to cut and/or cauterize tissue engaged by said first and second elements;
    an ultrasonically energized blade disposed at a distal end of said cutting element wherein said blade is moveable in a direction which is substantially parallel to a central axis of said shaft;
    an ultrasonic transducer coupled to said shaft, said transducer adapted to propagate ultrasonic vibrations along said shaft to said cutting element, said shaft and said cutting element ultrasonically isolated from said outer tube and said first and second elements, wherein said shaft and said transducer are moveable in a direction which is substantially parallel to said central axis of said shaft such that movement of said transducer and said shaft bring said ultrasonically energized blade into contact with tissue engaged by said first and second elements; and
    an electrical energy communication means for delivering electrical energy to said transducer to cause said transducer to vibrate an ultrasonic frequency.

5. The surgical instrument of claim 4 wherein said first and second elements are isolated from said ultrasonic vibration of said cutting element.

6. The surgical instrument of claim 4 wherein one of said first and second elements comprises a staple cartridge containing staples;

wherein said surgical instrument further comprises a staple driver arranged to extend into said cartridge to drive said staples out of said cartridge and through tissue engaged by said first and second elements; and wherein the other of said first and second elements comprises an anvil adapted to receive and close said staples driven from said cartridge through tissue engaged between said first and second elements.

7. A surgical instrument comprising:

an actuation end;

a hollow tube coupled to said actuation end;

an end effector extending distally from said tube;

said end effector comprising first and second elements;

an actuating element operatively coupled to at least one of said first and second elements, said actuating element arranged to move said at least one element towards the other of said first and second elements to engage tissue therebetween;

an opening extending longitudinally through said first element:

a shaft within said tube and ultrasonically isolated from said tube, said shaft having a distal end;

a cutting element coupled to said distal end of shaft;

an ultrasonically energized blade disposed at a distal end of said cutting element wherein said blade is moveable in a direction which is substantially parallel to a central axis of said shaft, said blade being adapted to be moved through said opening to cut and/or cauterize tissue engaged by said first and second elements; and an ultrasonic transducer coupled to said shaft, said transducer adapted to propagate ultrasonic vibrations to said cutting element, wherein said shaft and said transducer are moveable in a direction which is substantially parallel to said central axis of said shaft such that movement of said transducer and said shaft bring said ultrasonically energized blade into contact with tissue engaged by said first and second elements.

8. The surgical instrument of claim 7 wherein one of said first and second elements comprise a staple cartridge containing staples; and wherein the other of said first and second elements comprises an anvil adapted to receive and close staples driven from said cartridge through tissue engaged by said first and second elements.

9. The surgical instrument of claim 8 wherein said staples are arranged in at least one parallel row adjacent said opening.

10. The surgical instrument of claim 8 wherein said cutting element follows a cutting path defined by said opening, said cutting path having opposite longitudinal sides; and wherein said staples are arranged adjacent each of said sides of said cutting path.

* * * * *